United States Patent [19]

Witzel

[11] Patent Number: 4,832,691
[45] Date of Patent: May 23, 1989

[54] PNEUMATIC BOUGIE, PARTICULARLY FOR TREATMENT OF STENOSES

[76] Inventor: Lothar Witzel, DRK-Krankenhaus, Drontheimer Strasse 39, D-1000 Berlin, Fed. Rep. of Germany, 65

[21] Appl. No.: 25,223

[22] Filed: Mar. 12, 1987

[30] Foreign Application Priority Data

Mar. 25, 1986 [DE] Fed. Rep. of Germany ....... 3610091

[51] Int. Cl.$^4$ ............................................. A61M 29/00
[52] U.S. Cl. ....................................... 604/96; 128/344
[58] Field of Search ................. 128/344, 348.1, 207.15

[56] References Cited

U.S. PATENT DOCUMENTS

| | | | |
|---|---|---|---|
| 1,598,283 | 8/1926 | Kinney | 604/96 |
| 2,043,083 | 6/1936 | Wappler | 128/344 |
| 2,687,131 | 8/1954 | Raiche | 604/101 |
| 3,204,633 | 9/1965 | Hofstra | 604/246 |
| 3,509,884 | 5/1970 | Bell | 604/101 |
| 3,880,168 | 4/1975 | Berman | 128/207.15 |
| 3,882,852 | 5/1975 | Sinnreich | 128/344 |
| 3,913,565 | 10/1975 | Kawahara | 604/96 |
| 4,367,747 | 1/1983 | Witzel | 128/344 |
| 4,689,041 | 8/1987 | Corday et al. | 128/344 |

Primary Examiner—John D. Yasko

[57] ABSTRACT

The bougie has a balloon dilatator which is slipped over a gastroscope. The balloon dilatator comprises an inflatable balloon whose diameter is limited to a given upper value during inflation. The balloon homogeneously consists of a flexible material of little elasticity. It is shaped like a truncated cone. Through the balloon runs a flexible tube of a given length, and the balloon is attached to this tube. The tube's dimensions are such that the gastroscope may be passed therethrough. A conveyance tube opens into the balloon for inflation thereof. The conveyance tube is connected to a blood pressure manometer having a bleeding valve. By displacing the bougie, different diameters of the conical ballon may be placed in the constricted segment of the stomach-intestine region. When the balloon is inflated, the constricted element will be expanded to a predetermined diameter, thereby allowing for passage of ingested food.

17 Claims, 1 Drawing Sheet

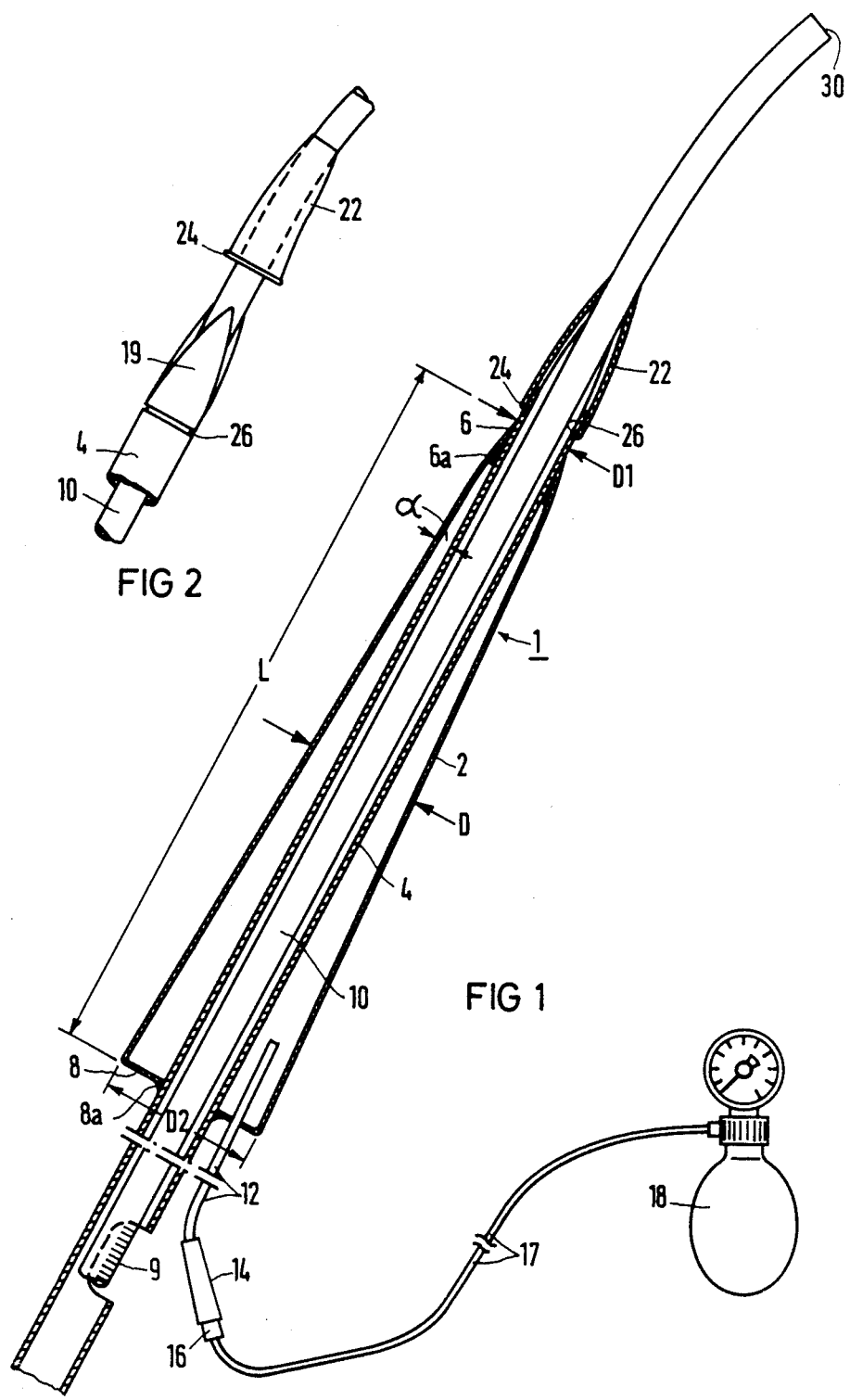

PNEUMATIC BOUGIE, PARTICULARLY FOR TREATMENT OF STENOSES

FIELD OF THE INVENTION

This invention relates to a pneumatic bougie for insertion into the stomach-intestine-region of a living being. Particularly, this invention relates to the treatment of stenoses in man. Still more particularly, this invention relates to a balloon dilatator having an inflatable balloon slipped over a flexible endoscope whose diameter is limited during the inflation to a given upper value, and to a device for inflating the balloon.

BACKGROUND OF THE INVENTION

In the field of medicine one distinguishes between different diseases in the stomach-intestine-region of a living being, among others between achalasia and stenosis.

The case of achalasia in man concerns the inability of the stomach entrance to open up to admit food. For the treatment of this disease devices have been developed, in particular dilatators, to "burst" the stomach entrance. After such treatment the stomach entrance stays open constantly. Food subsequently taken in falls into the stomach by force of gravity. A pneumatic dilatator for introduction into the esophagus and for the treatment of achalasia in man is described in my U.S. Pat. No. 4,367,747. In this dilatator a balloon is used whose diameter is limited during inflation to a given upper limiting value. The dilatator comprises a balloon of a flexible material of little elasticity and a flexible tube of a given length which is passed therethrough. During the treatment, a gastroscope is passed through the tube. For inflating the balloon, an inflation device is provided. This device contains a capillary tube which at one end opens into the balloon. The other end is connected to a commercial blood pressure manometer having a drain or bleeding valve.

An organic or functional stenosis, relating to an inability to swallow liquid or compact food, concerns a condition which is caused by a disease of the esophagus. Here one distinguishes between peptic stenoses, stenoses after cauterization, stenoses after long stomach intubations, stenoses after irradiation, stenoses after operative anastomases, as well as others. Such a stenosis is, for example, located at the entrance of the stomach, but can also be located at the exit of the stomach. Due to the developement of new instruments and suitable techniques, most of these stenoses can be treated without operation. Many such treatments can be performed without hospitalization, although some require a short stay in the hospital. The most common form of treatment utilizes a bougie. In the course of such treatment, through admission of the bougie, an enlargement of the stomach-intestine-region is brought about. During one or more sessions, the stenosis is expanded by using a bougie, whose diameter is, for example, between 13 and 17 mm. The insertion of the bougie occurs either or without sight-control by means of an endoscope.

In the prior art, a bougie is known which consists primarily of a Teflon tube, which at one point has a "swell-out" or expanded portion of about 15 mm and which is slipped over an endoscope. It is a disadvantage of this bougie that one can only expand a constricted segment to a fixed value of 15 mm and that the physician during the introduction has to push the afore-mentioned "swell-out" of 15 mm through the throat of the patient. This is unpleasant to the patient and entails a certain risk of injury. With such a bougie, one can expand only narrow parts of the esophagus, but not other parts in the stomach-intestine-region of the patient.

Furthermore, it is known to use rubber and mercury bougies which have a flexible, conically tapering tip. A disadvantage of these bougies is their blind introduction into the esophagus and consequently a certain danger of perforation. Also with such bougies only constricted areas in the esophagus can be treated.

Furthermore a so-called metal or ring bougie is known which is pushed over a guide wire. The ring bougie is guided by the guide wire to the constriction which is to be enlarged. It is considered a disadvantage of such a bougie that only stenoses in the esophagus can be treated. Besides, the treatment is a complicated and long procedure, and this can be a heavy burden to the patient. A certain danger of perforation exists in this case as well.

A pneumatic bougie of the type having an inflatable balloon slipped over an endoscope and having an inflation device is disclosed in the German periodical "Deutsches Ärzteblatt-Ärztliche Mitteilungen", volume 44, pages 27 to 30, Nov. 5, 1982, in prticular on page 28, right column, paragraph 2.

With such a pneumatic bougie the danger of perforation is decreased considerably. With such a device, the endoscope along with the dilatator is introduced into the cavity. Under sight-control they are pushed forward until the stenosis which is to be treated surrounds the dilatator. The balloon is slowly inflated to a pressure of 300 mm Hg, whereby the constricted segment is enlarged. The diameter of the balloon is limited to 15 mm. Unfortunately, it has turned out that one cannot work delicately or sensitively enough with such a device. The balloon, which is formed as a cylinder, rests in the stenosis during the inflation procedure. During treatment painful over-extensions can occur. Furthermore, with such an apparatus the treatment is limited to 15 mm, which corresponds to the diameter of the cylindricaL balloon.

SUMMARY OF THE INVENTION

1. Objects

It is an object of this invention to design a pneumatic bougie of the above described type which can easily be handled by a physician in a plurality of cases.

It is another object of the invention to provide a pneumatic bougie that allows for flexible handling, adapted to the individual cases.

It is still another object of the invention to provide a pneumatic bougie which allows for dilation of a constricted segment to an extent which corresponds to a selected one of a plurality of diameters.

2. Summary

The invention is based on the consideration that these objects can be met if a pneumatic bougie is provided that is conically shaped.

According to this invention, the pneumatic bougie comprises a balloon the material of which consists homogeneously of a flexible material of little elasticity. The balloon is formed in the shape of a truncated cone. A flexible tube of a given length is passed through the balloon, and the balloon is fastened to this tube. The tube's dimensions are such as to allow for the insertion of an endoscope. One end of a conveyance or capillary tube is connected to the balloon. Via this tube the balloon can be inflated. The other end of the conveyance tube is connected to a blood pressure manometer having a bleeding valve.

With this bougie, the advantages of a flexible rubber bougie having a conical tip are combined with the advantages of a pneumatic dilatator for the treatment of achalasia in man. The conically formed pneumatic bougie allows for a process which is not dangerous and easily endured by the patient during the treatment of narrow passages in the stomach-intestine-region, preferably in the esophagus. With this bougie, stenoses are enlarged under sight-control, whereby the bougie, given a certain pressure in the balloon, can be pushed into the stenosis by hand. Thus, there is added to the pneumatic pressure a delicately controllable pressure portion, which depends on the pushing forward of the conical balloon. Experiments have shown that quick and easy work is possible with such a bougie. It has also proven to be an advantage that a single conically formed bougie can be used for patients of different sizes and of different ages. The physician therefore does not need to store different bougie sizes, which simplifies stock-keeping considerably. It has also turned out that such a bougie can be used with good success in differently developed stenoses. Consequently, treatment in the large intestine as well as in the small intestine is possible.

In a preferred embodiment the balloon presents a diameter of at least 10 mm at one end and a diameter of at least 20 mm at the other end in its inflated condition. A further embodiment, which can also be used as a device for the treatment of achalasia in man and thus as a combination device, is characterized by the fact that the balloon presents a diameter of about 40 mm at said other end in its inflated condition. The afore-mentioned diameters are preferably obtained by an inner excess pressure which amounts to 200 to 300 mm Hg.

Preferably, the length of the bougie is approximately 10 cm in normal cases and approximately 30 cm for special purposes.

The foregoing and other objects, features and advantages of the invention will be apparent from the following more particular description of prefered embodiments of the invention, as illustrated in the accompanying drawings.

BRIEF DESCRIPTION OF THE DRAWINGS

In the drawings:

FIG. 1 represents a cross-section of a bougie in accordance with this invention, and FIG. 2 represents a side-view of the slit end of a tube, onto which a conically formed balloon is fastened.

DETAILED DESCRIPTION OF THE PREFERED EMBODIMENTS

In FIGS. 1 and 2, a pneumatic bougie 1 for the treatment of stenoses of man is shown. Principal item of this bougie 1 is an inflatable balloon 2, through which a relatively long and flexible tube 4 of a given length is passed. The balloon 2 is conically shaped or (expressed differently) shaped like a truncated cone. It is attached to the tube 4 in an air-tight fashion. For this purpose there is provided a first fastening point or location 6a at one end and a second fastening point or location 8a at the other (ring-shaped) end 8 of the balloon 2.

Balloon 2 consists of a flexible material, which is however, only slightly elastic after inflation. Such a material, for example, is polyurethane with a PVC-resin admixture. However, the inflatable balloon 2 may preferably consist of polyvinyl-chloride (PVC), as well as the tube 4. The fastening or connection at the points 6a, 8a is performed in an air-tight manner. The balloon 2 and the tube 4 may, for instance, be welded, glued or casted together at these points 6a, 8a. In particular, the thickness of the PVC foil of the balloon 2 lies between 0,3 and 0,8 mm.

In the inflated state, the balloon 2 has its first end 6 a diameter D1 of at least 10 mm and at its second end 8 a diameter D2 of at least 20 mm.

The length L of the balloon 2 is approximately 8 to 15 cm in the so-called "normal construction". Preferably, the length is about L=10 cm. The diameters D1 and D2 have typical values which are approximately D1=9 mm and D2=20 mm. Thereby one can slowly extend stenoses up to 20 mm, which (from the medical point of view) is enough in many cases. In exceptional cases it may be suitable to choose a value of about D2=25 mm. The afore-mentioned values D2=20 mm and, as the case may be, D2=25 mm correspond to an internal pressure of approximately 300 mm Hg. In this "normal construction" the balloon 2 is designed merely for the treatment of stenoses. In the so-called "special constructiion" the length L of the balloon 2, by way of example, may amount to 30 cm. In this case the balloon 2 in its fully inflated state may have a diameter D2 of about 40 mm at the other end 8. In this case, an enlargement or extension of about 10 mm up to 40 mm may be performed which is generally not only sufficient for stenoses but also for the treatment of achalasia in man. In this case, the bougie 1 can be considered as a combination device, which can be used for the treatment of stenosis as well as for the treatment of achalasia.

Experiments have shown that the conicaL shape of the balloon 2, with an acute or tapered angle alpha, advantageously may be dimensioned such that the diameter D of the balloon 2 increases 1 mm with each centimeter in the longitudinal direction of the tube 4. In this way, one can easily read a measuring scale 9 either outside of the tube 4 or, in case tube 4 is made of a transparent material, therethrough. The measuring scale 9 is arranged on a conventional gastroscope 10 of small diameter. Such a gastroscope 10 is a flexible endoscope for the examination of the stomach-intestine-region.

As already mentioned, the tube 4 may particularly consist of polyvenyl-chloride (PVC), but also, for example, of Teflon. Its interior is dimensioned for the reception of the gastroscope 10. In accordance with the outer diameter of the gastroscope 10, the tube 4 may have, for example, an internal diameter of 10 mm. There are also gastroscopes which have a smaller diameter, for instance 6 mm or 8 mm. Since the end of the tube 4 lies tightly at the inner wall of the gastroscope 10, which will be explained in more detail later on, the tube 4 may also have an internal diameter of 11 or 12 mm. The dimensions are chosen in such a way that the tube 4 fits well over the endoscope 10. After treatment it is pulled off and sterilized. A tube 4 having an internal diametere within the region of 10 to 12 mm fits well over a gastroscope 10 having a diameter of, for example, 6 mm, 8 mm or 10 mm. With the chosen dimension in the region of 10 to 12 mm one can utilize a gastroscope 10 which is adapted best to the intended application. The thickness of the wall of the tube 4 may be, for example, approximately 1 mm.

A conveyance or capillary tube 12, by which the balloon 2 is inflatable from outside, runs into the balloon 2. At one end this conveyance tube 12 is provided with an adapter 14. A coupling piece 16 fits into the adapter 14 in an air-tight manner. Coupling piece 17 is connected pneumatically via a tube 17 to a commercial blood pressure manometer 18 having a safety or bleeding valve. The blood pressure manometer 18 allows for inflating the balloon 2 to a certain pressure p (of, for example, p=300 mm Hg) after the introduction of the balloon 2 into the stomach-intestine-region of the patient and for maintaining this pressure p for some time. The pressure p should be within the region of 200 to 300 mm Hg. For reasons of stability and to insure a long life-time (longevity), it is suitable and prefered to have the conveyance tube 12 run into the balloon 2 at the rear end face 8 thereof, as illustrated. Instead of an end face 8 which is arranged vertically with respect to the longitudinal direction of the tube 4, an oblique end face 8 may also be provided.

From FIG. 1 it is evident that the tube 4 is passed over the gastroscope 10 during the treatment. FIG. 2 shows that the upper end piece 19 of the tube 4 is cut in a star-shaped manner in the longitudinal direction thereof. Altogether four parts or flaps are formed here. Therefore, this slit end piece 19 can easily be compressed by a cap 22, which is shown pulled off in FIG. 2. Consequently, the end piece 19 of the tube 4 is held in place on the gastroscope 10. This cap 22 is conically shaped and elastical, and, particularly, consists of a synthetic material. By means of this cap 22, one can affix or attach the tube 4 and consequently the balloon 2 at any selected part of the gastroscope 10 and also easily detach it therefrom. For instance, the cap 22 may have a length of only 35 mm; and it may have an upper internal diameter of 6 mm and a lower internal diameter of 12 to 14 mm. As illustrated, cap 22 contains a ring-shaped enforcement or pad 24 (which may be resilient) on its lower end. Pad 24 fits or locks in a ring-shaped groove 26 at the end 19 of the tube 4. In this way it is made sure that cap 22 cannot move or be shifted. In other words, pad 24 makes sure that the star-shaped end piece 19 of the tube 4 is pressed together until it assumes the diameter of the gastroscope 10. Instead of such a cap 22, a different kind of attachment may be chosen. Such attachment is also provided for holding the end piece 19 of the tube 4 close to the gastroscope 10. For instance, a ring of rubber may be chosen. The upper end of the tube 4 is located about 40 mm away from the end 6 of the balloon 2.

The movable tip 30 of the gastroscope 10, which points upwards in FIG. 1, includes a viewing window. During the treatment of a stenosis, the gastroscope 10 and the balloon 2 attached thereon are introduced throught the mouth into the esophagus of the patient at a pressure of p=0 mm Hg. During this procedure, the balloon 2 is attached tightly to the tube 4. The tube 4 and the balloon 2 are carefully pushed forward into the stenosis under sight-control by means of the gastroscope 10. The cap 22 hereby already exerts a certain stretching or bougie effect. At first the region at the end 6 of balloon 2 is placed in the stenosis. Then the balloon 2 is pumped up by means of the blood pressure manometer 18 until a pressure of approximately p=300 mm Hg is reached. It is important that during this procedure a slow expansion up to a given width D is obtained, for example up to D=16 mm. Through a jerky expansion, the stenosis might burst. Then the air is let out of the balloon 2, and the device is pushed forward a little bit farther into the stomach-intestine-region. This also occurs under sight-control. A width or depth control is performed by means of the measuring scale 9. Then the balloon 2 is again delicately and sensitively inflated by means of the blood pressure manometer 18. Hereby, the region of the stenosis is carefully expanded to an internal diameter of now, for example, 17 mm. Subsequently, the air is released again through the bleeding valve, and the balloon 2 is pushed farther forward. The depth reading from the measuring scale 9 is hereby a direct measure for the bougie diameter D which can be achieved at the stenosis with p=300 mm Hg. Afterwards, the balloon 2 is carefully inflated again, the air is subsequently released, etc. In this manner, a slow expansion of the stenosis is guaranteed. Through correct handling, the danger of perforation of the esophagus or another part of the stomach-intestine-region, for example of the just treated large intestine, can be avoided.

Cleaning of the bougie after use is very simple. After use it is taken apart. That is, the cap 22 is detached, and the gastroscope 10 is pulled out of the tube 4. The individual components are washed with warm water and soap, and the bougie is afterwards sterilized with gas.

While the form of the pneumatic bougie herein described constitutes a preferred embodiment of the invention, it is to be understood that the invention is not limited to this precise form of assembly, and that a variety of changes may be made therein without departing from the scope of the invention.

What is claimed is:

1. A pneumatic bougie for insertion into the stomach-intestine-region of a living being and for expanding a constricted segment thereof, particularly for the treatment of stenoses of man, comprising in combination:
    (a) a balloon dilatator for being slipped over a flexible endoscope, said balloon dilatator having a distal end and a proximal end and further having
        an inflatable balloon,
            which homogenously consists of a flexible material of little elasticity,
            whose diameter at any selected cross-section is thereby limited to a respective given upper value during inflation, and
            which is formed like a truncated cone, said cone having a first end face of a small diameter in the region of said distal end and a second end face of a large diameter in the region of said proximal end, and said cone having a plurality of diameters between said end faces,
        an inflation device for the inflation of said balloon, said inflation device having
            a blood pressure manometer including a bleeding valve, and
            a capillary tube connecting said manometer to said balloon for inflating said balloon and releasing air therefrom, and
    (b) a flexible tube of a given length,
        said flexible tube being dimensioned for passing said endoscope therethrough,
        said flexible tube being passed through said first and said second end face of said balloon,
        said flexible tube being attached to said balloon in the region of said first and said second end face in an air tight manner, and
        said flexible tube having a distal tube end and a distal tube end portion which is to be introduced into the living being, whereby said balloon can be placed in said constricted segment such that a selected diameter is assumed by said cone when said balloon is inflated, thereby expanding said constricted segment to a size corresponding to said selected diameter of said cone.

2. The bougie in accordance with claim 1, wherein said balloon in the inflated state has a diameter of at least 10 mm at said first end face and a diameter of at least 20 mm at said second end face.

3. The bougie in accordance with claim 2, wherein said balloon has a diameter of approximately 40 mm at said second end face in its inflated state.

4. The bougie in accordance with claim 1, wherein said truncated conical shape of said balloon is such that its diameter increases about 1 mm with each centimeter in the longitudinal direction of said flexible tube.

5. The bougie in accordance with claim 1, wherein the length of said balloon is approximately 100 mm in the longitudinal direction of said flexible tube.

6. The bougie in accordance with claim 1, wherein the length of said balloon is approximately 300 mm in the longitudinal direction of said flexible tube.

7. The bougie in accordance with claim 1, wherein a cap of an elastic material is fastened on said distal end portion of said flexible tube.

8. The bougie in accordance with claim 1, wherein said distal tube end (piece) of said flexible tube is located about 40 mm away from said first end face of said balloon.

9. The bougie in accordance with claim 1, wherein said distal tube end portion of said flexible tube is cut in a star-shaped way in the longitudinal direction thereof.

10. The bougie in accordance with claim 1, wherein said balloon is made of polyvinyl chloride (PVC).

11. The bougie in accordance with claim 10, wherein said flexible tube is made of polyvinyl chloride (PVC).

12. The bougie in accordance with claim 1, wherein said balloon reaches its application state in the form of a truncated cone at an inner pressure which is approximately 200 to 300 mm Hg in excess to ambient pressure.

13. The bougie in accordance with claim 1, further comprising a flexible endoscope passed through said flexible tube, and a measuring scale for measuring the depth of insertion in the stomach-intestine-region, said scale being applied to said endoscope.

14. The bougie in accordance with claim 1, wherein said (conveyance) capillary tube is connected to the second end face of said balloon.

15. The bougie in accordance with claim 1, wherein said blood pressure manometer along with said bleeding valve is a commercial medical instrument.

16. The bougie in accordance with claim 1, wherein said (conveyance) capillary tube is connected with said blood pressure manometer via adapter means.

17. The bougie in accordance with claim 1, wherein said flexible tube has an inner diameter in the range of 10 to 12 mm.

* * * * *